(12) United States Patent
Nagasawa et al.

(10) Patent No.: US 7,744,273 B2
(45) Date of Patent: Jun. 29, 2010

(54) THERMAL ANALYSIS APPARATUS

(75) Inventors: Kanji Nagasawa, Chiba (JP); Rintaro Nakatani, Chiba (JP)

(73) Assignee: SII Nanotechnology Inc., Chiba (JP)

( * ) Notice: Subject to any disclaimer, the term of this patent is extended or adjusted under 35 U.S.C. 154(b) by 260 days.

(21) Appl. No.: 11/841,400

(22) Filed: Aug. 20, 2007

(65) Prior Publication Data
US 2008/0279249 A1 Nov. 13, 2008

(30) Foreign Application Priority Data
Aug. 29, 2006 (JP) ............... 2006-232274

(51) Int. Cl.
G01N 25/00 (2006.01)
G01K 17/06 (2006.01)
G01K 3/06 (2006.01)

(52) U.S. Cl. ............ 374/31; 374/40; 374/141; 374/11; 374/137; 374/5; 374/132; 703/2

(58) Field of Classification Search ........... 374/5, 374/10–12, 29–39, 40, 100–112, 43–45, 374/135, 137, 141, 159, 178, 179, 163, 166–167, 374/130–134, 161; 436/147; 422/41; 432/128; 454/152; 118/696
See application file for complete search history.

(56) References Cited

U.S. PATENT DOCUMENTS

| 6,007,421 | A * | 12/1999 | Schwarz ............... 454/156 |
|---|---|---|---|
| 6,533,577 | B2 * | 3/2003 | Anderson et al. ........... 432/128 |
| 6,679,128 | B2 * | 1/2004 | Wanek et al. ............... 73/865.6 |
| 2002/0146657 | A1 * | 10/2002 | Anderson et al. ............. 432/11 |
| 2003/0160088 | A1 * | 8/2003 | Mitten et al. ................. 228/219 |
| 2004/0216470 | A1 * | 11/2004 | Thomas et al. ................. 62/63 |
| 2006/0117825 | A1 * | 6/2006 | Pfaffmann et al. ............. 72/60 |
| 2007/0258186 | A1 * | 11/2007 | Matyushkin et al. ........ 361/234 |
| 2008/0017104 | A1 * | 1/2008 | Matyushkin et al. ........ 118/696 |
| 2008/0175993 | A1 * | 7/2008 | Ashjaee et al. ......... 427/255.26 |

FOREIGN PATENT DOCUMENTS

| JP | H07-122619 B | 12/1995 |
|---|---|---|
| JP | 3066687 | 5/2000 |

* cited by examiner

Primary Examiner—Gail Verbitsky
(74) Attorney, Agent, or Firm—Brinks Hofer Gilson & Lione

(57) ABSTRACT

A thermal analysis apparatus possesses a temperature sensor measuring a temperature of a heating furnace inside, a temperature program setter which can set a temperature program and outputs a temperature program signal, a temperature control section adjusting a supply electric power to a heater in compliance with a difference between the temperature program signal and a detection signal of the temperature sensor, a processor section calculating an air flow rate corresponding to a program temperature, and a mass flow controller which adjusts an air flow rate supplied to the heating furnace inside in compliance with a signal of the air flow rate calculated by the processor section. In the processor section, operation expressions calculating the air flow rate are set so as to differ respectively in a higher temperature side and a lower temperature side than a predetermined boundary temperature.

3 Claims, 2 Drawing Sheets

THERMAL ANALYSIS APPARATUS

This application claims priority under 35 U.S.C.§119 to Japanese Patent Application Nos. JP2006-232274 filed Aug. 29, 2006, the entire content of which is hereby incorporated by reference.

BACKGROUND OF THE INVENTION

1. Field of the Invention

The present invention relates to a thermal analysis apparatus in which a heating furnace is cooled by a supply of a cooling gas.

2. Description of the Related Arts

Hitherto, in the thermal analysis apparatus such as differential scanning calorimeter, an analysis is performed by possessing the heating furnace, accommodating in its inside a sample (specimen), and measuring an egress-and-ingress of a heat of the sample with its heat quantity by changing a temperature of the sample by raising or lowering it using heating and cooling apparatuses. In the thermal analysis apparatus like this, there is one in which the heating furnace is temperature-controlled, e.g., by cooling the heating furnace by supplying a gas, which is cooled by a liquefied refrigerant, to the heating furnace, and heating the heating furnace by a heater provided in the heating furnace, or the like. In a case performing the cooling, there is one in which a control for flowing the cooling gas is performed by opening/closing, in compliance with a necessity, an electromagnetic valve provided between a liquefied refrigerant supply device and the heating furnace (e.g., refer to Japanese Patent No. 3066687 Gazette and JP-B-7-122619 Gazette).

Japanese Patent No. 3066687 is one in which the cooling of the heating furnace after a measurement finish in the thermal analysis apparatus is automated to thereby contrive a labor saving in a measurement and an improvement in an efficiency, and is one in which there is made such that, if a measurement finishes, the cooling of the heating furnace is automatically started by making the electromagnetic valve ON to thereby flow the cooling gas of a constant quantity, the cooling is automatically stopped if the heating furnace is cooled to a cooling stop temperature previously set and, in a case where a temperature of the heating furnace rises again by a thermal inertia or the like, it is cooled to or below a set temperature in a short time by automatically performing a re-cooling.

JP-B-7-122619 Gazette is one in which there is disclosed about a constitution of a full automatic gas cooling by liquefied nitrogen, one in which there is made such that there is previously set a temperature program in which a temperature change in regard to an elapse of time is programmed, there are performed, so as to follow that temperature program, a cooling control of a sample chamber (heating furnace) by a supply electric power regulator together with the elapse of time, and a temperature control of the sample chamber by a heating of the heater, and one in which a temperature of the sample chamber is precisely controlled from a temperature lower than a chamber temperature, which reaches to a liquefied refrigerant temperature, to a high temperature of about 700° C.

However, in the thermal analysis apparatus used in the Patent Documents 1 and 2, there are issues like the below.

In Japanese Patent No. 3066687 Gazette and JP-B-7-122619 Gazette, if cooled by flowing the cooling gas to the heating furnace becoming such a high temperature as to exceed 700° C. for instance, there is an issue that the heating furnace comprising ceramic is cracked and damaged by a thermal influence exerted on the heating furnace. Therefore, generally, it is lowered by a natural cooling to about 700° C. deemed to be a temperature, at which the heating furnace is not cracked, from such a high temperature as to exceed the above 700° C. and, after the heating furnace becomes 700° C. or below, the cooling gas is supplied to the heating furnace. However, depending on the measurement, there is such a demand that it is desired to measure by lowering the temperature faster than the natural cooling in a higher temperature region than the above 700° C., so that a suitable cooling method is requested.

Further, in a case controlled only by ON/OFF of the electromagnetic valve like Japanese Patent No. 3066687 Gazette and JP-B-7-122619 Gazette, as mentioned above if cooled by opening the electromagnetic valve at a time point becoming 700° C. or below, it follows that the temperature of the heating furnace rapidly lowers, and there is a defect that a quick change in the temperature makes a feedback control of the heater difficult, so that there is a drawback that a precise temperature control of the heating furnace is impossible. Therefore, there is an issue that an accurate measurement result is not obtained.

The present invention is one made in view of the issues mentioned above, and its object is to provide a thermal analysis apparatus made so as to cool the temperature of the heating furnace without damaging the heating furnace by supplying the cooling gas of a suitable flow rate.

SUMMARY OF THE INVENTION

In order to achieve the above object, in a thermal analysis apparatus concerned with the present invention, it is a thermal analysis apparatus possessing a heating furnace, and a heater heating an inside of the heating furnace, and is characterized by possessing a temperature detector measuring a temperature of the heating furnace inside, a temperature program setter which can set a temperature program making a temperature change, of the heating furnace inside, complying with an elapse of time and outputs a temperature program signal, a temperature control section adjusting a supply electric power to the heater in compliance with a difference between the temperature program signal and a detection signal of the temperature detector, a processor section calculating a cooling gas flow rate corresponding to a program temperature of the temperature program, and a cooling gas flow rate adjustment section which is connected to the temperature program setter through the processor section, and adjusts a cooling gas flow rate supplied to the heating furnace inside in compliance with a signal of the cooling gas flow rate calculated by the processor section, and in that, in the processor section, operation expressions calculating the cooling gas flow rate are set so as to differ respectively in a higher temperature side and a lower temperature side than a predetermined boundary temperature, and the cooling gas flow rate calculated by the operation expression in the higher temperature side is made a degree in which the heating furnace is not damaged.

In the present invention, a suitable cooling gas flow rate is found according to the elapse of time of the temperature program, a signal is outputted to the cooling gas flow rate adjustment section, the cooling gas flow rate adjustment section is adjusted, and a cooling gas of predetermined quantity is supplied to the heating furnace and thus it can be cooled. And, when the program temperature becomes a higher temperature region than a predetermined boundary temperature, by supplying the cooling gas flow rate of small quantity of the degree in which the heating furnace is not damaged to the heating furnace, it is possible to cool it faster than the natural cooling. Further, when it is in a lower temperature region than the predetermined boundary temperature, it is possible to supply the cooling gas flow rate of large quantity to the heating furnace.

Further, in a thermal analysis apparatus concerned with the present invention, it is desirable that, at the program temperature, the operation expression in the higher temperature side than the boundary temperature makes a first operation expression, and the operation expression in the lower temperature side makes a second operation expression, and cooling gas flow rate curves found from each of the first operation expression and the second operation expression are connected by a cooling gas flow rate curve found from a third operation expression making a differential continuity.

In the present invention, since the cooling gas flow rate curves found from each of the first operation expression and the second operation expression are connected while gently continuing by the cooling gas flow rate curve basing on the third operation expression having the differential continuity, from the fact that it is possible to realize a cooling having no rapid temperature change, a temperature control of the heater in the temperature control section can be precisely performed, so that it is possible to obtain an accurate measurement data.

Further, in a thermal analysis apparatus concerned with the present invention, it is desirable that the boundary temperature is 600-800° C.

In the present invention, a temperature range of 600-800° C. is set as the degree in which the heating furnace is not damaged, and it can be supplied to the heating furnace with the cooling gas flow rate being changed in a case of the higher temperature side than this boundary temperature and a case of the lower temperature side than the same.

Further, in a thermal analysis apparatus concerned with the present invention, it is desirable that the boundary temperature is 700° C.

In the present invention, 700° C. is set as the degree in which the heating furnace is not damaged, and it can be supplied to the heating furnace with the cooling gas flow rate being changed in the case of the higher temperature side than this boundary temperature and the case of the lower temperature side than the same.

According to the thermal analysis apparatus of the present invention, it is possible to flow it to the heating furnace with the cooling gas flow rate of small quantity when the program temperature is in the higher temperature region than the boundary temperature, and flow it with the cooling gas flow rate of large quantity when it is in the lower temperature region than the boundary temperature. Accordingly, in the higher temperature region than the boundary temperature, by supplying the cooling gas of the degree, in which the heating furnace is not damaged, to the heating furnace, it is possible to cool faster than the natural cooling. Therefore, the temperature range, of the heating furnace, supplying the cooling gas becomes wide, so that there is brought about such an advantage that it is possible to perform a wider range measurement.

Further, in the higher temperature side than the boundary temperature, since the cooling gas flow rate of the degree in which the heating furnace is not damaged by the cooling is calculated by the processor section, it is possible to nullify such a fact that, like the prior art, the heating furnace is damaged by being rapidly cooled.

Moreover, from the fact that a suitable cooling gas flow rate can be supplied to the heating furnace on the basis of the temperature program, it is possible to perform a precise temperature control.

DESCRIPTION OF THE PREFERRED EMBODIMENTS

Figure 1:
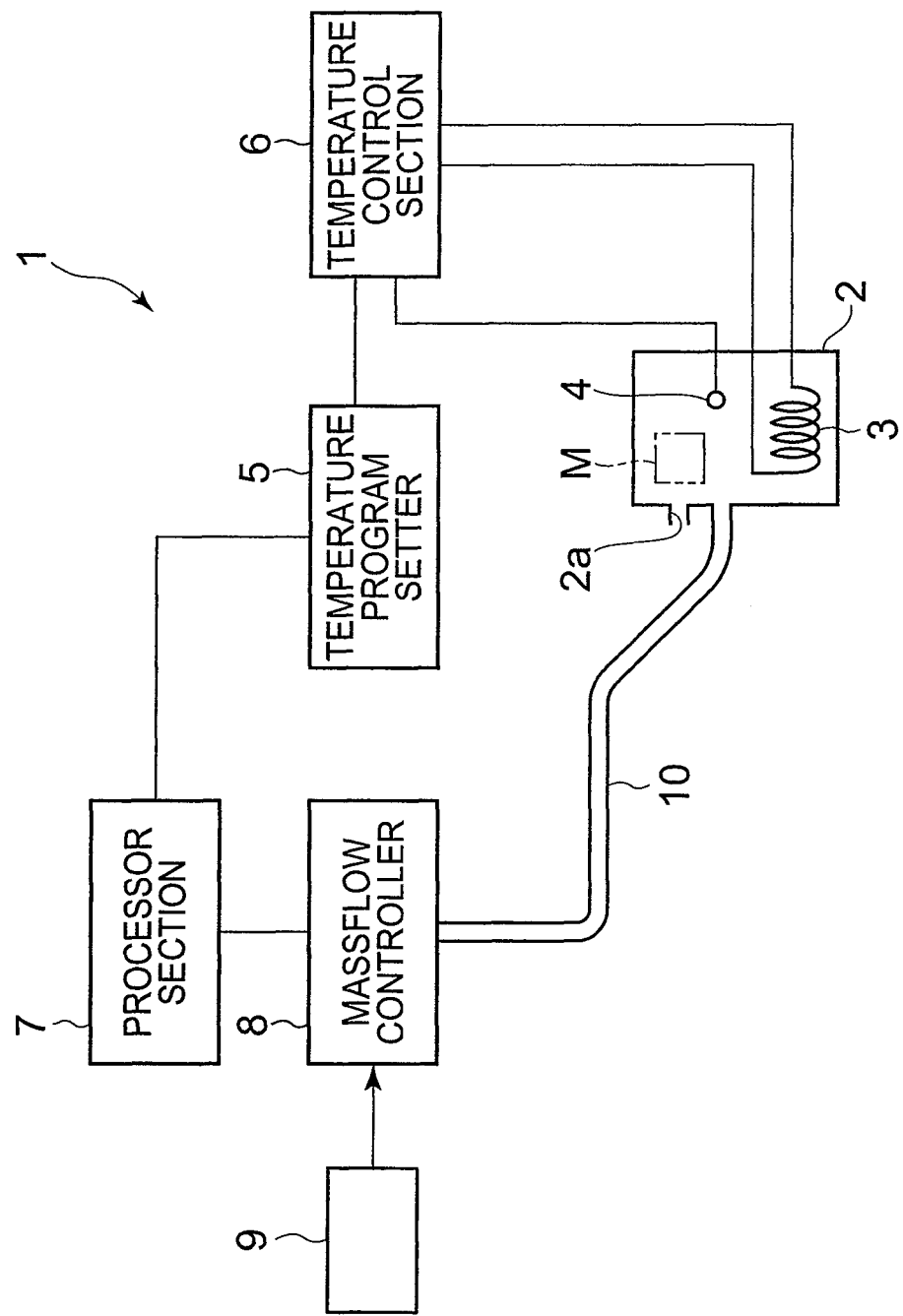
FIG. 1 is a block diagram explaining a whole epitome of a thermal analysis apparatus by an embodiment of the present invention.
Figure 2:
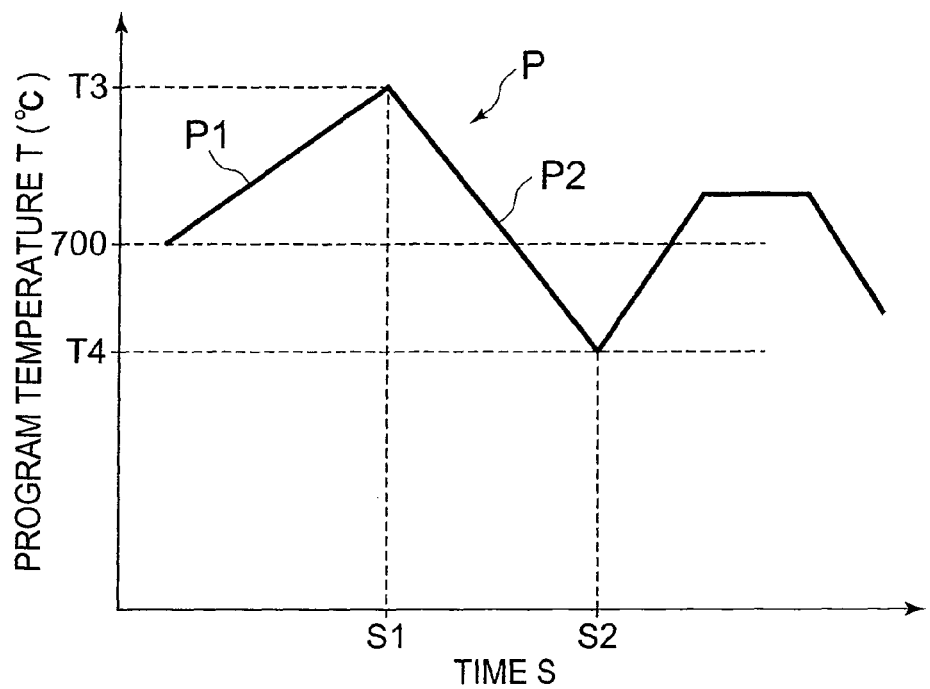
FIG. 2 is a diagram showing a temperature program set by a temperature program setter.
Figure 3:
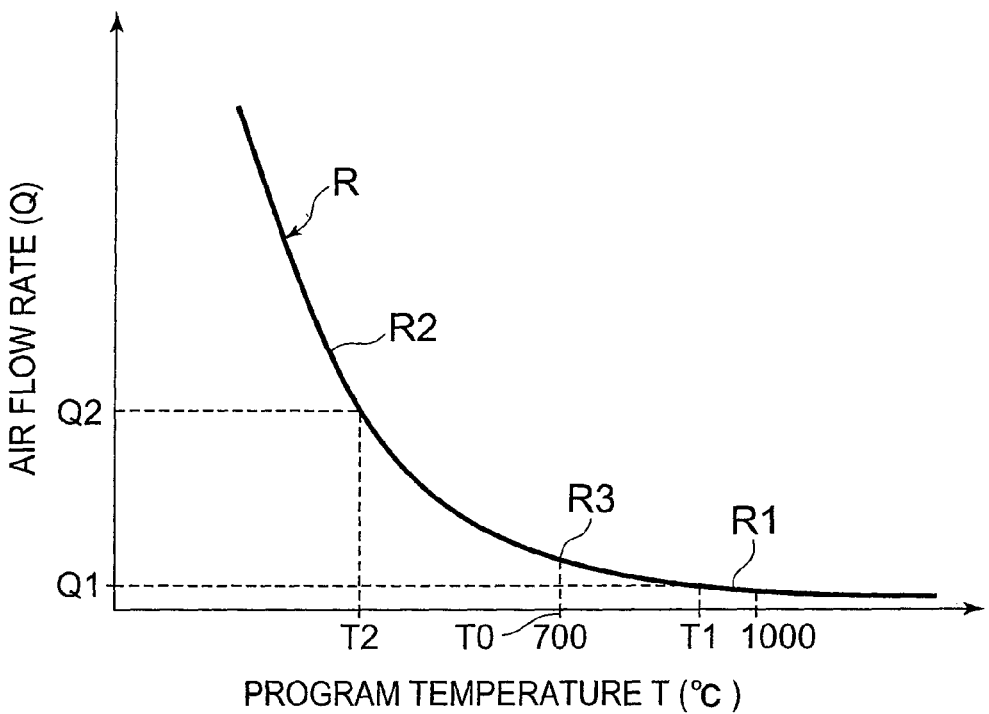
FIG. 3 is a graph showing a relation between a program temperature and an air flow rate.

Hereunder, about a thermal analysis apparatus by an embodiment of the present invention, there is explained on the basis of FIG. 1 to FIG. 3.

FIG. 1 is a block diagram explaining a whole epitome of the thermal analysis apparatus by the embodiment of the present invention, FIG. 2 is a diagram showing a temperature program set by a temperature program setter, and FIG. 3 is a graph showing a relation between a program temperature and an air flow rate.

As shown in FIG. 1, the thermal analysis apparatus by the present embodiment is one adopted in a thermal analysis apparatus 1 such as a differential scanning calorimeter capable of measuring a quantity of egress-and-ingress of a heat by performing a thermal analysis in order to detect a physical property change (structural phase transition, thermal denaturation, fusion, crystallization, or the like) occurring in a matter by a temperature change, a thermobalance detecting a weight change of the matter, and the like.

First, about a schematic constitution of the thermal analysis apparatus 1 by the present embodiment, there is explained on the basis of the drawing.

As shown in FIG. 1, the thermal analysis apparatus 1 by the present embodiment possesses a heating furnace 2 accommodating a sample M (specimen) becoming a measurement object and a reference sample (diagrammatic representation is omitted) making a thermally inert reference matter, and a heater 3 for raising a temperature of the heating furnace 2. And, there is measured a thermal flow rate making entrance and egress to and from the sample M per unit time by detecting a temperature difference between the sample M and the reference sample while raising or lowering the temperature of the heating furnace 2 by temperature-controlling the heater 3.

Additionally, the thermal analysis apparatus 1 is schematically constituted by a temperature sensor 4 (temperature detector) measuring the temperature of the heating furnace 2 inside, a temperature program setter 5 capable of setting a temperature program P (refer to FIG. 2) and outputting a temperature program signal, a temperature control section 6 connected to the temperature program setter 5, the temperature sensor 4 and the heater 3 and adjusting a supply electric power to the heater 3 in compliance with a difference between the temperature program signal and a detection signal of the temperature sensor 4, a processor section 7 calculating an air flow rate (cooling gas flow rate) corresponding to a program temperature of the temperature program P, and a mass flow controller 8 (cooling gas flow rate adjustment section) connected to the temperature program setter 5 through the processor section 7 and adjusting the air flow rate supplied to the heating furnace 2 inside in compliance with a signal of the processor section 7.

The heating furnace 2 shown in FIG. 1 makes a furnace body for high temperatures, and can raise a heating temperature to, e.g., about 2000° C. in maximum. Further, the heater 3 is a heating means for heating the heating furnace 2 in such a manner as mentioned above, and it is possible to adopt, e.g., an electrically heated heater disposed like a coil so as to surround a side face periphery of the heating furnace 2, or the like.

And, the heater 3 and the temperature sensor 4 of the heating furnace 2 inside are connected to the temperature program setter 5 through the temperature control section 6. The temperature control section 6 is one controlling so as to adjust the supply electric power to the heater 3 in compliance with a difference (temperature difference signal) between an output signal of the temperature program P of the temperature program setter 5 and an output signal of the temperature sensor 4.

Additionally, about an action of the temperature control section 6, there is explained more detailedly. The temperature control section 6 shown in FIG. 1 is one which precisely temperature-controls such that, in regard to the temperature difference signal between the temperature program setter 5 and the temperature sensor 4, the heating furnace 2 follows the temperature program P set in the temperature program setter 5 by feeding back an electric power value, which is obtained as a result of a well-known PID (proportion/integration/differential) control operation, to the heater 3. In other words, if the temperature of the heating furnace 2 becomes lower than a temperature set by the temperature program P, a heating quantity by the heater 3 is increased and, if the temperature of the heating furnace 2 is too high, the heating quantity is decreased. And, in a case where this temperature of the heating furnace 2 is lowered to a temperature lower than a room temperature or the temperature is rapidly lowered, it is possible to air-cool by supplying the air to the heating furnace 2 inside by using the mass flow controller 8 (detailedly, mentioned later).

Further, the temperature control of the heating furnace 2 by the temperature control section 6 is always performed irrespective of an existence/nonexistence of an operation of the mass flow controller 8, and the temperature control is performed in a wide range from a low temperature to a high temperature (e.g., in the present embodiment, about 2000° C. in maximum).

The temperature program setter 5 shown in FIG. 1 is one which can set a temperature pattern (i.e., "temperature program P" shown in FIG. 2) changing (raising or lowering) the temperature of the heating furnace 2 inside together with the elapse of time, and outputs, from the temperature program setter 5, a temperature signal which is program-set.

Here, the temperature program P shown in FIG. 2 is constituted by a time S in abscissa axis and a program temperature T (° C.) in ordinate axis, shows a temperature change determined in regard to the time, and makes a target value for measuring the sample M. That is, in the present thermal analysis apparatus 1, it follows that the temperature control section 6 and the mass flow controller 8 are controlled so as to follow the temperature program P. Incidentally, the temperature program P shown in FIG. 2 is one example of a temperature rise/drop in regard to the measurement of the sample M, and can be arbitrarily set by a measurement person while depending on measurement conditions and the like.

As shown in FIG. 1, the mass flow controller 8 is connected to the temperature program setter 5, and one adjusting an air flow rate supplied from a gas supply section 9 in compliance with an output signal of the temperature program setter 5 (accurately, the processor section 7), thereby supplying it to the heating furnace 2 inside. Here, in the thermal analysis apparatus 1, there is provided a gas pipe line 10 for supplying the gas to the heating furnace 2 inside from the gas supply section 9 through the mass flow controller 8.

Incidentally, the gas supply section 9 is, e.g., an air compressor or the like, and a compressed air sent out of the gas supply section 9 is sent to the heating furnace 2 inside while passing through the gas pipe line 10. And, in the heating furnace 2, there is provided an air discharge port 2a.

Like this, by adopting the air compressor in the gas supply section 9 and using, in a cooling source, the compressed air by the compressor, which can be supplied only by an electric power, it becomes unnecessary to replenish a refrigerant, such as liquefied nitrogen for instance, to a tank. Additionally, detailedly although mentioned later, in a case of the air cooling, from the fact that it becomes an ordinary temperature in comparison with the low temperature refrigerant, it is possible to perform a cooling in which such a thermal influence as to damage the heating furnace 2 is made small even if it is in a high temperature region (e.g., temperature higher than 700° C.). Moreover, since the cooling control by the air cooling is not large in its temperature difference like the refrigerant, there is brought about such an advantage that the temperature control becomes easy to be performed.

Further, the mass flow controller 8 has a flow rate control valve (diagrammatic representation is omitted) in which a control is possible at a high accuracy by a digital control and, detailedly although mentioned later, becomes a constitution in which the flow rate control valve is adjusted according to an output signal of an air flow rate corresponding to the program temperature T (° C.) of the temperature program P set by the processor section 7.

Incidentally, the controls of the temperature program setter 5, the processor section 7 and the mass flow controller 8 are made open-loop controls, and not ones in which the temperature of the heating furnace 2 inside is controlled by being fed back to the processor section 7 and the mass flow controller 8.

Next, about a constitution of the processor section 7, and the like, there are explained on the basis of the drawings.

As shown in FIG. 1, the processor section 7 is connected to the temperature program setter 5, and a control device performing the control by calculating the air flow rate sent out of the gas supply section 9, which corresponds to the program temperature T (° C.) of the temperature program P (refer to FIG. 2), and transmitting an output signal of the calculated air flow rate to the mass flow controller 8.

Concretely, in the processor section 7, there is set an operation expression (function) for calculating an air flow rate Q corresponding to the program temperature T inputted from the temperature program setter 5, i.e., an operation expression in which the temperature and a cooling velocity are made parameters. FIG. 3 is one in which, on the basis of that operation expression, a relation between the program temperature T (° C.) and the air flow rate Q is made a graph. Here, this graph is made an air flow rate curve, and made a sign R.

This air flow rate curve R is one for calculating a suitable air flow rate according to the program temperature of the temperature program P in order to air-cool the heating furnace 2 and, with 700° C. being made a boundary temperature T0, a temperature region in a higher temperature side than this boundary temperature T0 and a temperature region in a lower temperature side than the boundary temperature T0 are set by different operation expressions.

In other words, in a case of a temperature higher than the boundary temperature T0, it is denoted by a first operation expression R1 in which it becomes a slight flow rate of a degree in which the heating furnace 2 is not cracked and damaged and, in a case of a temperature lower than the boundary temperature T0, it is denoted by a second operation expression R2 making such a quadratic curve that the airflow rate increases together with, e.g., a drop of the program temperature. Additionally, the air flow rate curves found from each of the first operation expression R1 and the second operation expression R2 are mutually connected, in the vicinity of the boundary temperature T0 or change points of both the air flow rate curves, with a gentle curve having a continuity by an air flow rate curve found from a third operation expression R3 making a function having a differential continuity.

Here, the boundary temperature T0 (about 700° C.) is deemed to be a temperature exerting the thermal influence on a ceramic furnace core of the heating furnace 2.

By this, when the program temperature is in a higher temperature region (e.g., a temperature T1 shown in FIG. 3) than the boundary temperature T0, it can be flowed to the heating furnace 2 with an air flow rate (Q1) of small quantity and, when it is in a lower temperature region (e.g., a temperature T2 shown in FIG. 3) than the boundary temperature T0, it can be flowed to the heating furnace 2 with an air flow rate (Q2) of large quantity. Accordingly, in the present thermal analysis apparatus 1, it is possible to cool the heating furnace 2, which is in the temperature region from the temperature higher than 700° C. to 700° C., faster than the natural cooling, and it is possible to perform the temperature control by supplying a suitable air flow rate to the heating furnace 2 on the basis of the temperature program P.

Additionally, in the vicinity of the boundary temperature T0, since the air flow rate curves found from each of the first operation expression R1 and the second operation expression R2 are connected while gently continuing by the air flow rate curve basing on the third operation expression R3, which has the differential continuity, from the fact that a cooling having no rapid temperature change can be realized, it is possible to precisely perform a temperature control of the heater 3 in the temperature control section 6, so that it is possible to obtain an accurate measurement data.

Like this, by setting the air flow rate curve R corresponding to the program temperature, there is found the suitable air flow rate Q following upon the elapse of time of the temperature program P, a signal is outputted to the mass flow controller 8, the mass flow controller 8 is adjusted, and the compressed air of a predetermined quantity is supplied to the heating furnace 2 and thereby it is air-cooled.

Next, about operations of the thermal analysis apparatus 1 by the present embodiment, there are explained on the basis of FIG. 1 to FIG. 3.

First, the desired temperature program P shown in FIG. 2 is previously set in the temperature program setter 5 (refer to FIG. 1). If the temperature program setter 5 is operated, a temperature signal is outputted from the temperature program setter 5. In a case where the temperature signal by the temperature program P becomes a temperature rise (sign P1 shown in FIG. 2), the temperature of the heating furnace 2 becomes a temperature T3 from 700° C. at a time S1 by the operation of the heater 3.

And, in a case where a certain predetermined time elapses and the temperature signal by the temperature program P becomes a temperature drop (sign P2 shown in FIG. 2), a temperature management of the heating furnace 2 is performed with the heater 3 maintaining its operation state, and a temperature signal of the temperature program setter 5 is inputted to the processor section 7. And, at this time, to the mass flow controller 8, there is outputted a signal of the air flow rate calculated, in a temperature region from the temperature T3 to 700° C., in the processor section 7 on the basis of the first operation expression R1 shown in FIG. 3 or, in a temperature region from 700° C. to a temperature T4, similarly on the basis of the second operation expression R2, and it follows that the air of a predetermined quantity is supplied to the heating furnace 2 and thus it is air-cooled. And, about the temperature rise/drop of the temperature program P after the temperature T4 at a time S2, the mass flow controller 8 is controlled by operations similar to those mentioned above.

As mentioned above, in the thermal analysis apparatus by the present embodiment, it is possible to flow it to the heating furnace with the air flow rate of small quantity when the program temperature T is in the higher temperature region than the boundary temperature T0, and flow it with the air flow rate of large quantity when it is in the lower temperature region than the boundary temperature T0. Accordingly, in the higher temperature region than the boundary temperature T0, by supplying the air of the degree, in which the heating furnace 2 is not damaged, to the heating furnace 2, it is possible to cool faster than the natural cooling. Therefore, the temperature range, of the heating furnace 2, supplying the air becomes wide, so that there is brought about such an advantage that it is possible to perform the wider rage measurement.

Further, in the higher temperature side than the boundary temperature T0, since an air flow rate of the degree in which the heating furnace 2 is not damaged by the cooling is calculated by the processor section 7, it is possible to nullify such a fact that, like the prior art, the heating furnace is damaged by being rapidly cooled.

Moreover, from the fact that a suitable air flow rate can be supplied to the heating furnace 2 on the basis of the temperature program P, it is possible to perform the precise temperature control.

In the above, although there is explained about the mode of the thermal analysis apparatus by the present invention, the present invention is not one limited to the above embodiment, and it can be suitably modified in a scope not deviating from its gist.

For example, in the present embodiment, although 700° C. is made the boundary temperature T0, it is not one numerically limited to this 700° C., and it is possible to cause its temperature range of the boundary temperature T0 to have a predetermined range. For example, there is deemed that it does not matter if the boundary temperature T0 is a range of 600-800° C.

Further, in the present embodiment, although the air flow rate is controlled by using the mass flow controller 8 in which the digital control is possible, there may be made such that, by using a well-known flow rate control valve, its opening/closing quantity is controlled.

Additionally, in the present embodiment, as the cooling method, although there is adopted an air-cooling system by the compressed air, it is not limited to this, and it does not matter if there is made so as to use a cooling gas such as liquefied nitrogen for instance.

What is claimed is:

1. A thermal analysis apparatus comprising:
a heating furnace;
a heater heating an inside of the heating furnace;
a temperature detector measuring a temperature of the heating furnace inside;
a temperature program setter which can set a temperature program making a temperature change, of the heating furnace inside, complying with an elapse of time and outputs a temperature program signal;

a temperature control section adjusting a supply electric power to the heater in compliance with a difference between the temperature program signal and a detection signal of the temperature detector;

a processor section calculating a cooling gas flow rate corresponding to a programmed temperature of the temperature program; and a cooling gas flow rate adjustment section which is connected to the temperature program setter through the processor section, and adjusts a cooling gas flow rate supplied to the heating furnace inside in compliance with a signal of the cooling gas flow rate calculated by the processor section, wherein in the processor section, operation expressions calculating the cooling gas flow rate are set so as to differ respectively in a higher temperature side and a lower temperature side than a predetermined boundary temperature, and the cooling gas flow rate calculated by the operation expression in the higher temperature side is made a degree that does not damage the heating furnace;

wherein the temperature program set by the program setter comprises:

a first operation expression on the higher temperature side;

a second operation expression on the lower temperature side, and wherein cooling gas flow rate curves found from each of the first operation expression and the second operation expression are connected by another cooling gas flow rate curve found from a third operation expression such that the entire cooling gas flow curves maintain continuity.

2. A thermal analysis apparatus according to claim 1, characterized in that the predetermined boundary temperature is 600-800° C.

3. A thermal analysis apparatus according to claim 1, characterized in that the predetermined boundary temperature is 700° C.

* * * * *